US010166181B2

(12) United States Patent
Ducrey et al.

(10) Patent No.: US 10,166,181 B2
(45) Date of Patent: Jan. 1, 2019

(54) SLOW RELEASE PHARMACEUTICAL COMPOSITION MADE OF MICROGRANULES

(75) Inventors: Bertrand Ducrey, Martigny (CH); Patrick Garrouste, Saxon (CH); Catherine Curdy, Riehen (CH); Marie-Anne Bardet, Maracon (CH); Herve Porchet, Cugy (CH); Eija Lundstrom, Lutry (CH); Frederic Heimgartner, Marin-Epagnier (CH)

(73) Assignee: Debiopharm Research & Manufacturing SA (CH)

( * ) Notice: Subject to any disclaimer, the term of this patent is extended or adjusted under 35 U.S.C. 154(b) by 249 days.

(21) Appl. No.: 12/601,649

(22) PCT Filed: Jun. 6, 2008

(86) PCT No.: PCT/IB2008/052241
§ 371 (c)(1),
(2), (4) Date: Apr. 20, 2010

(87) PCT Pub. No.: WO2008/149320
PCT Pub. Date: Dec. 11, 2008

(65) Prior Publication Data
US 2011/0052717 A1 Mar. 3, 2011

(30) Foreign Application Priority Data

Jun. 6, 2007 (EP) ..................................... 07109767
Oct. 27, 2007 (WO) .................. PCT/IB2007/054372

(51) Int. Cl.
*A61K 9/14* (2006.01)
*A61K 9/00* (2006.01)
*A61K 9/16* (2006.01)
*A61K 9/19* (2006.01)
(52) U.S. Cl.
CPC .......... *A61K 9/0019* (2013.01); *A61K 9/1647* (2013.01); *A61K 9/19* (2013.01)
(58) Field of Classification Search
None
See application file for complete search history.

(56) References Cited

U.S. PATENT DOCUMENTS

| 4,897,268 | A | * | 1/1990 | Tice ..................... A61K 9/1647 424/422 |
| 4,954,298 | A | | 9/1990 | Yamamoto |
| 5,134,122 | A | | 7/1992 | Orsolini |
| 5,192,741 | A | | 3/1993 | Orsolini et al. |
| 5,225,205 | A | | 7/1993 | Orsolini |
| 5,330,767 | A | | 7/1994 | Yamamoto |
| 5,445,832 | A | * | 8/1995 | Orsolini ............... A61K 9/1647 424/489 |
| 5,480,656 | A | | 1/1996 | Okada |
| 5,540,937 | A | | 7/1996 | Billot et al. |
| 5,575,987 | A | | 11/1996 | Kamei |
| 5,643,607 | A | | 7/1997 | Okada |
| 5,716,640 | A | | 2/1998 | Kamei |
| 5,776,885 | A | | 7/1998 | Orsolini et al. |
| 5,945,128 | A | * | 8/1999 | Deghenghi ........... A61K 9/0024 264/4.1 |
| 6,475,507 | B1 | | 11/2002 | Pellet et al. |
| 2001/0026804 | A1 | * | 10/2001 | Boutignon ............ A61K 9/0024 424/422 |
| 2002/0013273 | A1 | | 1/2002 | Shirley et al. |
| 2004/0170665 | A1 | | 9/2004 | Donovan |
| 2006/0110460 | A1 | | 5/2006 | Ferret et al. |
| 2007/0031500 | A1 | * | 2/2007 | Cherif-Cheikh ..... A61K 9/0024 424/486 |
| 2007/0059363 | A1 | * | 3/2007 | Lee et al. ...................... 424/468 |

FOREIGN PATENT DOCUMENTS

| GB | 2 257 909 | 1/1993 |
| JP | 1-121222 | 5/1989 |
| JP | 3-66625 | 3/1991 |
| JP | 6-87758 | 3/1994 |

(Continued)

OTHER PUBLICATIONS

"Development of a single-shot subunit vaccine for HIV-1: Part 4. Optimizing microencapsulation and pulsatile release of MN rgp120 from biodegradable microspheres," Cleland, J., et al., Journal of Controlled Release 47: 135-150 (1997).*
"Microencapsulation techniques using ethyl acetate as a dispersed solvent: effects of its extraction rate on the characteristivs of PLGA microspheres," Sah, H., Journal of Controlled Release 47: 233-245 (1997).*
Sun, Z., et al., "Particle Size Specifications for Solid Oral Dosage Forms: A Regulatory Perspective," American Pharmaceutical Review 13(4) (2010), as accessed from http://www.americanpharmaceuticalreview.com/Featured-Articles/36779-Particle-Size-Specifications-for-Solid-Oral-Dosage-Forms-A-Regulatory-Perspective/ on Jan. 5, 2017.*

(Continued)

*Primary Examiner* — David J Blanchard
*Assistant Examiner* — Daniel F. Coughlin
(74) *Attorney, Agent, or Firm* — Sterne, Kessler, Goldstein & Fox P.L.L.C.

(57) ABSTRACT

Pharmaceutical composition made of microparticles for the slow release of an active substance at least during a period covering the 6th month after injection of said composition, said composition comprising a group of microparticles made of a copolymer of the PLGA type which incorporate an active substance in the form of a water insoluble peptide salt; said copolymer furthermore comprising at least 75% of lactic acid and an inherent viscosity between 0.1 and 0.9 dl/g, as measured in chloroform at 25° C. and at a polymer concentration of 0.5 g/dL; said microparticles furthermore having a size distribution defined as follows: —D (v,0.1) is between 10 and 30 micrometers, —D (v,0.5) is between 30 and 70 micrometers, —D (v,0.9) is between 50 and 1 10 micrometers.

4 Claims, 3 Drawing Sheets

(56) References Cited

FOREIGN PATENT DOCUMENTS

Figure 1:
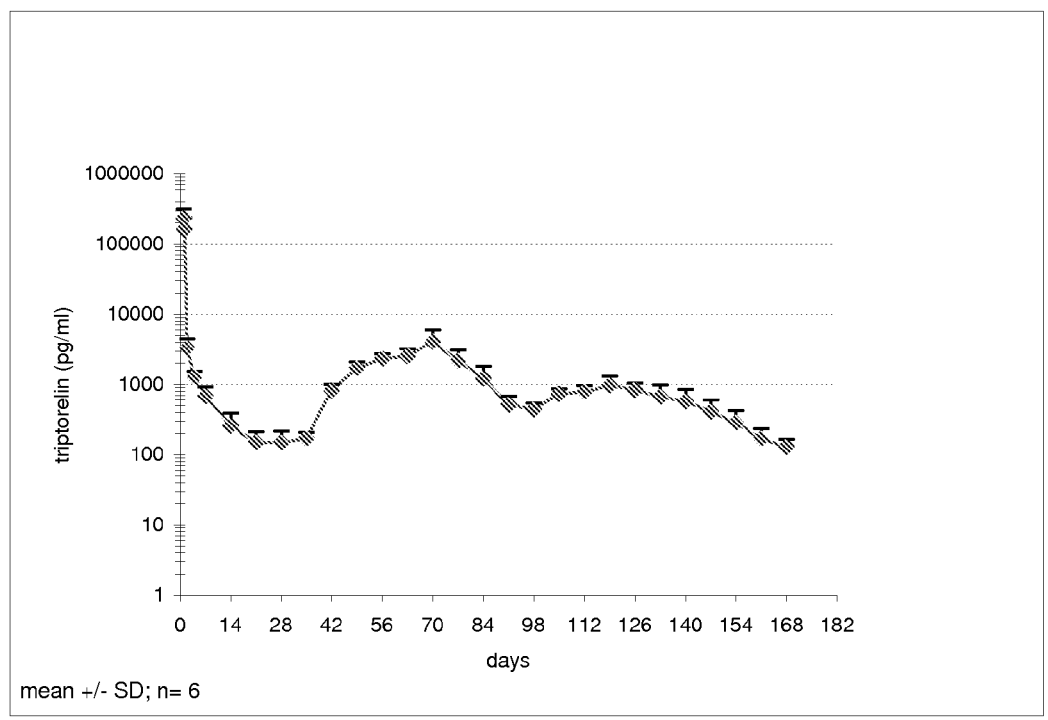

| JP | 2001-522812 | 11/2001 | | |
|---|---|---|---|---|
| JP | 2002-500631 | 1/2002 | | |
| JP | 2005-509611 | 4/2005 | | |
| WO | WO 95/11008 | * | 4/1995 | ............ A61K 39/39 |
| WO | WO 99/24061 | 5/1999 | | |
| WO | 2004/096259 | 11/2004 | | |
| WO | WO 2007/071395 A1 | 6/2007 | | |

OTHER PUBLICATIONS

Ravivarapu, H., et al., "Polymer and microsphere blending to alter the release of a peptide from PLGA microspheres," European Journal of Pharmaceutics and Biopharmaceutics 50: 263-270 (2000).*
Triptorelin, accessed from the Internet on Feb. 6, 2017 from https://en.-wikipedia.org/wiki/Triptorelin.*
Inherent Viscosity vs Molecular Weight, accessed from the Internet on Feb. 6, 2017 from http://www.absorbables.com-/technical/inherent_viscosity.html.*
Brandau, T., et al., "Microencapsulation and industrial application for uniform controlled release particles," XVIth International Conference on Bioencapsulation, Dublin Ireland, Sep. 4-8, 2008.*
International Search Report for PCT/IB2008/052241, dated Dec. 9, 2008.
International Preliminary Report on Patentability for PCT/IB2008/052241, dated Apr. 6, 2009.
Written Opinion of the International Searching Authority, dated Dec. 9, 2008.
Office Action issued in Japanese Patent Application No. 2010-510946, dated Feb. 19, 2013.
English translation of JP Office Action issued in Japanese Patent Application No. 2010-510946, dated Feb. 19, 2013.
Siegel et al, "Effect of drug type on the degradation rate of PLGA matrices", European Journal of Pharmaceutics and Biopharmaceutics 64 (2006) 287-293.
Giri et al, "Prospects of pharmaceuticals and biopharmaceuticals loaded microparticles prepared by double emulsion technique for controlled delivery", Saudi Pharmaceutical Journal (2013) 21, 125-141.
Arbor Pharmaceuticals, LLC Press Release, Debiopharm Group, "Arbor Pharmaceuticals, LLC and Debiopharm International SA Announce Commercial Availability of Triptodur™, Triptorelin 6-month Formulation, for Treatment of Central Precocious Puberty (CPP)", Oct. 3, 2017.
Debiopharm Group Press Release, "Debiopharm moves towards a new 6-Month formulation of Decapeptyl® to further help prostate cancer patients", Sep. 25, 2008.
Acknowledgement of receipt; Notice of Opposition; European Patent No. EP 2 164 467 (Application No. EP 08763237.8); Debiopharm Reseach & Manufacturing SA; Opponent: Generics [UK] Ltd.; Title: Slow Release Pharmaceutical Compositon Made of Micropaticles; dated Sep. 13, 2017.
Minkov et al, "A phase II trial with new triptorelin sustained release formulations in prostatic carcinoma", International Urology and Nephrology 33: 379-383; 2001.
Declaration of Helsinki (1964), "Recommendations guiding physicians in biomedical research involving human subjects", British Medical Journal, No. 7070, vol. 313, Dec. 7, 1996 (4 pages).
Kirk-Othmer, Encyclopedia of Chemical Technology, fourth Edition, vol. 22, Silicon Compounds to Succinic Acid and Succinic Anhydride, Copyrigh © 1997 by John Wiley & Sons, Inc., pp. 256-278.
Müller et al, "Pharmacokinetics of triptorelin after intravenous bolus administration in healthy males and in males with renal or hepatic insufficiency", Br J Clin Pharmacol 1997; 44:335-341.
Wang et al, "Characterization of the initial burst release of a model peptide from poly(D,L-lactide-co-glycolide) microspheres", Journal of Controlled Release 82 (2002) 289-307.
Elkington + Fife; Notice of Opposition of Generics [UK] Ltd; European Patent No. EP 2 164 467 (Application No. EP 08763237. 8); Debiopharm Reseach & Manufacturing SA; Opponent: Generics [UK] Ltd.; Title: Slow Release Pharmaceutical Compositon Made of Micropaticles; letter dated Sep. 13, 2017 (14 pages).
Notice of opposition to a European patent; European Patent No. EP 2 164 467 (Application No. EP 08763237.8); Debiopharm Reseach & Manufacturing SA; Opponent: Generics [UK] Ltd.; Title: Slow Release Pharmaceutical Compositon Made of Micropaticles; form dated Sep. 13, 2017 (5 pages).
Acknowlegement of Receipt; European Patent No. 2 164 467 (Application No. EP 08763237.8); Opponent: Ferring B.V.; Title: Slow Release Pharmaceutical Composition Made of Microparticles; dated Sep. 14, 2017.
9th International Symposium on GnRH Analogues; The hypothalamic-pituitary-gonadal axis in cancer and reproduction; Feb. 10-12, 2008, E. Lundstrom, D. Purcea et al Berlin, Germany (3 pages).
Light Scattering Theory, Laser Diffraction (Static Light Scattering), Explore the future, 2007 HORIBA Ltd. (35 pages).
Wischke et al, "Principles of encapsulating hydrophobic drugs in PLA/PLGA microparticles", International Journal of Pharmaceutics 364 (2008) 298-327.
PLGA Wikipedia; From Wikipedia, the free encyclopedia; Aug. 31, 2017 cited by opponent Ferring B.V. as "May 16, 2008 version" (2 pages); Retrieved from "https://en.wikipedia.org/w/index.php?title=PLGA&oldid=212843253".
Poly(DL-Lactide-co-Glycolide) Mitsui PLGA Series, Jun. 2010; Bioabsorbable Polymer; Mitsui Chemicals (16 pages).
Statement of Opposition of Ferring B.V.; letter dated Sep. 14, 2017; Opposition to European Patent No. 2164467; Patentee: Debiopharm Research & Manufacturing SA; Title: Slow Release Pharmaceutical Composition Made of Microparticles (18 pages).
Notice of opposition to a European patent; European Patent No. 2164467 (Application No. EP 08763237.8); Patentee: Debiopharm Research & Manufacturing SA; Opponent: Ferring B.V.; Title: Slow Release Pharmaceutical Composition Made of Microparticles (5 pages).
Press Release, Jan. 11, 2016, Debiopharm International SA and Arbor Pharmaceuticals, LLC announce their US commercialization partnership for Triptorelin in Central Precocious Puberty.
Press Release, Jun. 30, 2017, Debiopharm International SA and Arbor Pharmaceuticals, LLC Announce U.S. FDA Approval for Triptodur™, Triptorelin 6-month Formulation, in the Treatment of Central Precocious Puberty (CPP).
Press Release, Jan. 13, 2014, Debiopharm Group™ Announces Completion of Recruitment for Phase III Clinical Study with Triptorelin 22.5 mg in Central Precocious Puberty.
Press Release, May 19, 2015, Debiopharm International SA Announces Phase III Positive Results for Triptorelin 6-month Formulation in the Management of Central Precocious Puberty (CPP).
Press Release, Jan. 9, 2017, Debiopharm Group's Triptorelin 6-month Formulation Receives Approval for the Treatment of Central Precocious Puberty (CPP) in Europe.
Press Release, Oct. 13, 2009, Ipsen and Debiopharm Group announce that Decapeptyl® (triptorelin embonate) 6-month successfully completes the European Decentralised Procedure for the treatment of locally advanced or metastatic prostate cancer, Developed by Debiopharm Group, triptorelin embonate 6-month will be commercialised by Ipsen in Europe.
Press Release, Feb. 4, 2010, Launch of Ipsen's Decapeptyl® 6-month formulation (LP 22.5 mg) in France for the treatment of locally advanced or metastatic hormone-dependent prostate cancer.
Press Release, May 27, 2014, Orient EuroPharma and Debiopharm Group™ announce their partnership and the launch of Pamorelin® LA in Singapore.
Press Release, Sep. 30, 2014, Trelstar® Six-Month Dosing for Prostate Cancer Patients Launches in Canada Trelstar® one-, three-, and six-month dosing options now available.
Press Release, Dec. 4, 2015, United Laboratories Inc. and Debiopharm International SA announce the launch of Pamorelin® LA in the Philippines.
Press Release, May 11, 2009, Debiopharm and Mepha sign distribution agreement for Pamorelin® LA 1- 3- and 6-month formulations—a new treatment for prostate cancer patients in Switzerland.

(56) References Cited

OTHER PUBLICATIONS

Press Release, Nov. 14, 2008, Debiopharm announces U.S. NDA filing of Trelstar® 6-month formulation for locally advanced or metastatic prostate cancer.

Press Release, Feb. 12, 2008, Clinical Update—Decapeptyl®/Trelstar® 6-Month Formulation—In Advanced Prostate Cancer—Presentation of Efficacy and Safety Phase III Results.

Klein K, et al. Efficacy and safety of triptorelin 6-month formulation in patients with central precocious puberty. J Pediatr Endocrinol Metab. 2016;29(11):1241-1248.

Triptodur™ web site—Oct. 12, 2017—Arbor Pharmaceuticals Inc. ClinicalTrials.gov web site re ClinicalTrials.gov Identifier: NCT01467882—Efficacy, Safety, and Pharmacokinetics (PK) of Triptorelin 6-month Formulation in Patients With Central Precocious Puberty—Sponsor: Debiopharm International SA—printed Oct. 12, 2017.

Lundstrom et al. "Triptorelin 6-Month Formulation in the Management of Patients with Locally Advanced and Metastatic Prostate Cancer an Open-Label, Non-Comparative, Multicentre, Phase III Study" Clin Drug Investig 2009; 29 (12): 757-765.

* cited by examiner

SLOW RELEASE PHARMACEUTICAL COMPOSITION MADE OF MICROGRANULES

This application is the U.S. national phase of International Application No. PCT/IB2008/052241, filed 6 Jun. 2008, which designated the U.S. and claims priority to European Application No. 07109767.9, filed 6 Jun. 2007, and International Application No. PCT/IB2007/054372, filed 27 Oct. 2007, the entire contents of each of which are hereby incorporated by reference.

FIELD OF INVENTION

The invention relates to pharmaceutical compositions made of microparticles which are used for the slow release of an active substance.

It more precisely relates to such compositions which comprise a copolymer of lactic and glycolic acid (PLGA) incorporating, as active substance, a water insoluble peptide salt.

STATE OF THE ART

Compositions as defined above are disclosed in Swiss patent CH 679 207 A5.

DEFINITIONS

In the present text, the term "microparticle" has to be understood as a solid object of any shape, e.g. microsphere or microgranule, having a median diameter of less than 250 micrometers.

The expression D (v,0.5), also mentioned as "median diameter", means that 50 of the microparticles have a diameter which is less than the indicated value. Hence, if D (v,0.5)=55 micrometers, 50% of the microparticles have a diameter which is less than 55 micrometers.

In the same way, D (v,0.1) means that 10% of the microparticles have a diameter which is less than the indicated value and D (v,0.9) means that 90% of the microparticles have a diameter which is less than the indicated value.

All above values are measured by laser diffraction.

The term "microgranule" refers to an object which is the result of a milling operation on an elongated product such as an extrudate.

The term PLGA XX/YY refers to a poly(D,L lactide-co-glycolide), where XX represents the lactide content, and YY represents the glycolide content. The ratio lactide/glycolide being expressed in mol percent.

The term "month" refers to 28 days.

GENERAL DESCRIPTION OF THE INVENTION

The objective of the invention is to offer several improvements with respect to the state of the art.

One of those improvements is to provide a continuous and efficient slow release of the active substance during at least a period covering the $6^{th}$ month after injection of the composition.

To this effect the invention concerns a pharmaceutical composition made of microparticles for the slow release of an active substance at least during a period covering the $6^{th}$ month after injection of said composition, said composition comprising a group of microparticles made of a copolymer of the PLGA type which incorporate an active substance in the form of a water insoluble peptide salt; said copolymer furthermore comprising at least 75% of lactic acid and an inherent viscosity between 0.1 and 0.9 dl/g, as measured in chloroform at 25° C. and at a polymer concentration of 0.5 g/dL; said microparticles furthermore having a size distribution defined as follows:
  D (v,0.1) is between 10 and 30 micrometers,
  D (v,0.5) is between 30 and 70 micrometers,
  D (v,0.9) is between 50 and 110 micrometers.

In a first embodiment, the composition consists of one single group of microparticles. In that case the lactide content of the PLGA is of at least 85% and the inherent viscosity is between 0.1 and 0.4 dl/g.

A release during at least 6 months can be obtained with the composition of this first embodiment.

The microparticles may be microspheres or microgranules.

In a second embodiment, the composition comprises a group of microparticles wherein the lactide content of the PLGA is of at least 85% and the inherent viscosity is preferably between 0.5 and 0.9 dl/g and more preferably between 0.63 and 0.67 dl/g.

The microparticles may be microspheres or microgranules

The group of microparticles defined in the second embodiment may advantageously be used for providing a slow and significant release during at least a period starting from the $4^{th}$ month after injection of the composition until and including the $6^{th}$ month.

In a third embodiment, the pharmaceutical composition furthermore comprises another group of microparticles made of a copolymer of the PLGA type having a lactide content between 70% and 80% which incorporates said active substance.

Both groups of microparticles may be present in a dose ratio (expressed in peptide content) close to 50:50.

The inherent viscosity of each group is between 0.5 and 0.9 dl/g.

Preferably the inherent viscosity of the other group is between 0.60 and 0.70 dl/g and in particular 0.65 dl/g and the inherent viscosity of the first group is the same as the one defined in the second embodiment.

The microparticles of the other group may be microgranules or microspheres.

Advantageously both groups of microparticles are microgranules.

One group of microparticules is advantageously obtained by mixing, in a solvent-free process, said PLGA with said water insoluble peptide salt.

When two groups of microparticles are present, one group may be used to provide a slow and significant release of the water insoluble peptide salt during at least the first three months after injection of the composition while the other group is used for a release starting from the $4^{th}$ month.

In a preferred embodiment the active substance is a LHRH agonist triptorelin (used as water insoluble salt such as the pamoate salt thereof) which may be efficiently used in the treatment of prostate cancer.

The LHRH agonist triptorelin is released in an important immediate amount within hours following injection and then shows a constant and significant release over a long period of at least 168 days, i.e. 6 months

DETAILED DESCRIPTION OF THE INVENTION

Figure 2:
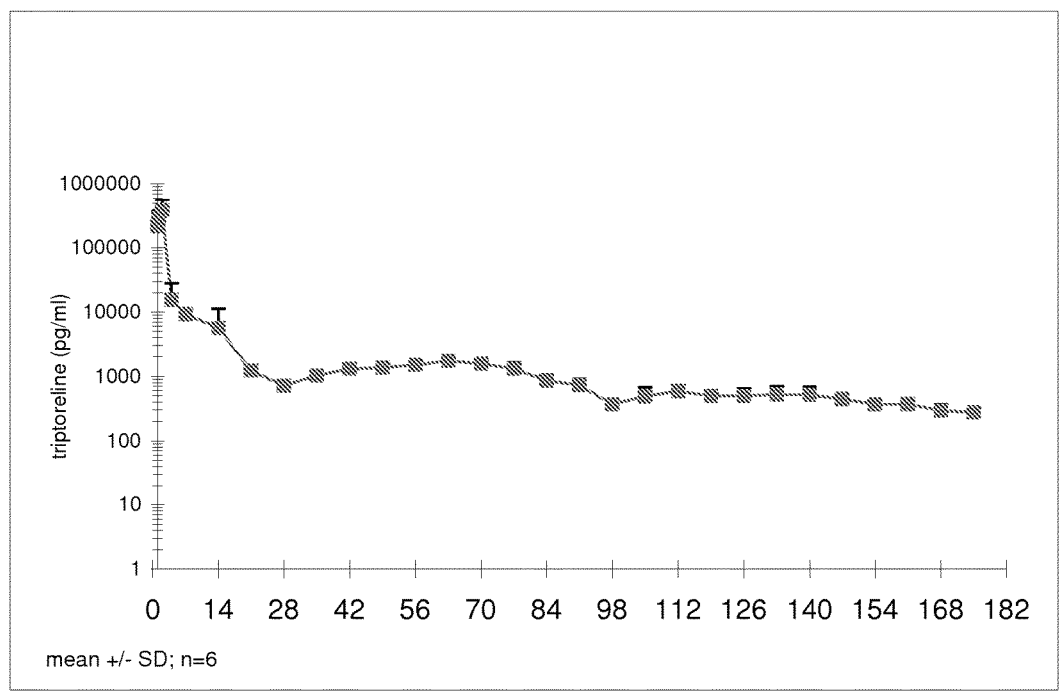
Figure 3:
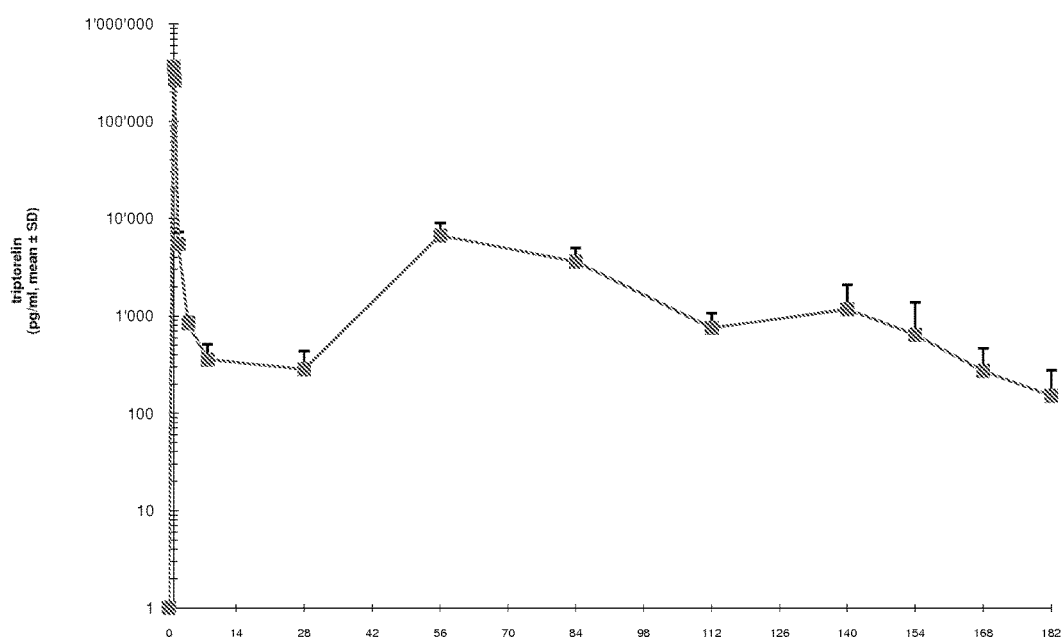

The invention is discussed below in a more detailed way with examples, the first being illustrated by the following figure:

FIG. 1 shows triptorelin, LHRH agonist, serum levels obtained with the pharmaceutical biodegradable composition of example 1, FIG. 2 shows triptorelin, LHRH agonist, serum levels obtained with the pharmaceutical biodegradable composition of example 3, FIG. 3 shows triptorelin, LHRH agonist, serum levels obtained with the pharmaceutical biodegradable composition of example 4, In the following examples the viscosity is expressed in dl/g and is measured at a polymer concentration of 0.5 g/dl.

EXAMPLE 1

A formulation of microgranules of triptorelin pamoate is prepared with the following process.

Approximately 12% (w/w) of triptorelin pamoate is mixed with approximately 88% (w/w) PLGA 75/25 having a viscosity of 0.65 dl/g, at room temperature. The given mixture is duly homogenized, subjected to progressive compression and simultaneously to a progressive heating, before extrusion. The extrudate is cut into pellets and ground at a temperature of about −100° C. The microgranules obtained after grinding are sieved below 180 micrometers. Their size distribution is defined as follows:

D (v,0.1)=23 micrometers
D (v,0.5)=55 micrometers
D (v,0.9)=99 micrometers

A formulation of microspheres of triptorelin pamoate and PLGA 85/15 having an inherent viscosity of 0.68 dl/g is prepared as follows:

Aqueous phase is prepared by mixing, under magnetic stirring, at a temperature of 40° C., 240 g of polyvinyl alcohol and 11760 g of purified water. In parallel, the organic phase is prepared by total dissolution of 12 g of polymer 85/15 poly(D,L lactide-co-glycolide) (PLGA) in 45 g of ethyl acetate under magnetic stirring.

3000 mg of triptorelin pamoate are suspended in 30 g of ethyl acetate and placed under magnetic stirring. This solution is incorporated to the organic phase previously prepared. The organic phase is then introduced in a homogenisation chamber simultaneously with the said aqueous phase. Both phases are mixed in order to obtain an emulsion and the extraction of the solvent from the organic phase and to isolate a suspension of microspheres.

Finally the formulation of microspheres is recovered by filtration and dried by lyophilization.

The microspheres have a size distribution defined as follows:

D (v,0.1)=15.6 micrometers
D (v,0.5)=33.4 micrometers
D (v,0.9)=60.8 micrometers The formulation of microspheres and the formulation of microgranules are mixed in a vial in order to have a 50:50 dose ratio of each formulation. The mixture is suspended in an appropriate aqueous medium, lyophilised and sterilized by gamma irradiation.

The purity measured on the obtained pharmaceutical biodegradable composition is 98.3% and the burst evaluated in vitro (in a phosphate buffer pH 7.4) over a 6 hours period is 22.1%.

In this example, the obtained pharmaceutical formulation is tested in vivo and the animal model is the rat. The formulation as described above is suspended in water for injection and is administered at a concentration dose of 18 mg/kg to 6 rats.

The LHRH agonist triptorelin of said pharmaceutical biodegradable composition is released in an important immediate amount within hours following injection and then shows a constant and significant release over a long period of at least 168 days, i.e. 6 months.

EXAMPLE 2

A formulation of microgranules of triptorelin pamoate is prepared as described in example 1.

A formulation of microspheres of triptorelin pamoate is prepared as described in example 1 with PLGA 90/10 having an inherent viscosity of 0.7 dl/g. The microspheres have a size distribution defined as follows:

D (v,0.1)=17.6 micrometers
D (v,0.5)=39.9 micrometers
D (v,0.9)=84.2 micrometers The formulation of microspheres and the formulation of microgranules are mixed in a vial in order to have a 50:50 dose ratio of each formulation. The mixture is suspended in an appropriate aqueous medium, lyophilised and sterilized by gamma irradiation.

The purity measured on the obtained pharmaceutical biodegradable composition is 98.3% and the burst evaluated in vitro (in a phosphate buffer pH 7.4) over a 6 hours period is 19.4%.

The LHRH agonist triptorelin of said pharmaceutical biodegradable composition is released in an important immediate amount within hours following injection and then shows a constant and significant release over a long period of at least 168 days, i.e. 6 months.

EXAMPLE 3

A formulation of microgranules of triptorelin pamoate is prepared as described in example 1.

Another formulation of microgranules is prepared as described in example 1 with PLGA 85/15 having an inherent viscosity of 0.66 dl/g.

Approximately 20% (w/w) of triptorelin pamoate is mixed with approximately 80% (w/w) PLGA 85/15 at room temperature. The given mixture is duly homogenized, subjected to progressive compression and simultaneously to a progressive heating, before extrusion. The extrudate is cut into pellets and ground at a temperature of about −100° C. The microgranules obtained after grinding are sieved below 180 micrometers. Their size distribution is defined as follows:

D (v,0.1)=20.5 micrometers
D (v,0.5)=51.7 micrometers
D (v,0.9)=96.9 micrometers The 2 formulations of microgranules are mixed in a vial in order to have a 50:50 dose ratio of each formulation. The mixture is suspended in an appropriate aqueous medium, lyophilised and sterilized by gamma irradiation.

The purity measured on the obtained pharmaceutical biodegradable composition is 98.8% and the burst evaluated in vitro (in a phosphate buffer pH 7.4) over a 6 hours period is 45.0%.

In this example, the obtained pharmaceutical formulation is tested in vivo and the animal model is the rat. The formulation as described above is suspended in water for injection and is administered at a concentration dose of 18 mg/kg to 6 rats.

The LHRH agonist triptorelin of said pharmaceutical biodegradable composition is released in an important immediate amount within hours following injection and then shows a constant and significant release over a long period of at least 168 days, i.e. 6 months (see FIG. 2).

EXAMPLE 4

A formulation of microspheres of triptorelin pamoate and PLGA 95/5 having an inherent viscosity of 0.18 dl/g is prepared as follows:

Aqueous phase is prepared by mixing, under magnetic stirring, at a temperature of 40° C., 800 g of polyvinyl alcohol and 40 L of purified water. In parallel, the organic phase is prepared by total dissolution of 80 g of PLGA 95/5 in 334 g of isopropyl acetate under magnetic stirring.

20 g of triptorelin pamoate are suspended in 100 g of isopropyl acetate and placed under magnetic stirring. This solution is incorporated to the organic phase previously prepared. The organic phase is then introduced in a homogenisation chamber simultaneously with the said aqueous phase. Both phases are mixed in order to obtain an emulsion and the extraction of the solvent from the organic phase and to isolate a suspension of microspheres.

Finally the formulation of microspheres is recovered by filtration and dried by lyophilization.

The microspheres have a size distribution defined as follows:
D (v,0.1)=17.8 micrometers
D (v,0.5)=37.1 micrometers
D (v,0.9)=74.8 micrometers This formulation of microspheres is suspended in an appropriate aqueous medium, lyophilised and sterilized by gamma irradiation.

The purity measured on the obtained pharmaceutical biodegradable composition is 99.2% and the burst evaluated in vitro (in a phosphate buffer pH 7.4) over a 6 hours period is 10.9%.

In this example, the obtained pharmaceutical formulation is tested in vivo and the animal model is the rat. The formulation as described above is suspended in water for injection and is administered at a concentration dose of 18 mg/kg to 6 rats.

The LHRH agonist triptorelin of said pharmaceutical biodegradable composition is released in an important immediate amount within hours following injection and then shows a constant and significant release over a long period of at least 168 days, i.e. 6 months (see FIG. 3).

EXAMPLE 5

In order to increase patients' compliance and convenience the inventors also developed a formulation as defined in previous example 3 which allows one injection every 6 Months (24 Weeks). The study discussed in this example investigated the efficacy and safety of this formulation after 2 consecutive intramuscular injections of triptorelin pamoate 22.5 mg in 120 patients with advanced prostate cancer. Four-weekly testosterone assessments were performed over 48 weeks.

Serum testosterone concentrations fell to castrate levels (≤1.735 nmol/L) in 97.5% of the patients on D29, and 93% of the patients maintained castration from Week 8 to 48. Five out of 8 patients who escaped castration had only an isolated testosterone breakthrough without rising PSA (Prostate Specific Antigen), indicating maintained efficacy. Only one of these isolated breakthroughs was a true "acute-on-chronic" phenomenon after the second injection.

The median relative decreases in PSA from baseline were 96.9% at Week 24, and 96.4% at Week 48, when 80.9% of patients had a normal PSA.

The type and incidence of AEs (Adverse Events) were comparable with those observed with the registered triptorelin formulations. As with other GnRH agonists, the most frequent drug related AEs were hot flushes (71.7% of patients). The study drug was very well tolerated locally.

The study discussed above shows that Triptorelin 6-Month formulation is efficacious and safe in inducing chemical castration in patients with advanced prostate cancer. This new convenient formulation requires only 1 injection every 24 weeks, and shows comparable efficacy and safety with the marketed 1- and 3-Month formulations.

The invention claimed is:

1. A pharmaceutical composition of microgranules comprising 22.5 mg triptorelin in the form of triptorelin pamoate, wherein the pharmaceutical composition comprises: a) a first formulation of microgranules comprising approximately 20% (w/w) of triptorelin pamoate mixed with approximately 80% (w/w) PLGA, wherein the PLGA in the first formulation contains approximately 85% lactide and 15% glycolide; and b) a second formulation of microgranules comprising approximately 12% (w/w) triptorelin pamoate mixed with approximately 88% (w/w) poly(D,L lactide-co-glycolide) (PLGA), wherein the PLGA in the second formulation contains approximately 75% lactide and 25% glycolide, wherein the triptorelin is released from the pharmaceutical composition in an immediate amount within hours following injection and then constantly released over a period of at least 168 days.

2. The pharmaceutical composition of claim 1, wherein the first formulation of microgranules and the second formulation of microgranules are mixed to have a 50:50 dose ratio of triptorelin.

3. The pharmaceutical composition of claim 2, wherein the pharmaceutical composition induces chemical castration in patients over a six-month period of time.

4. The pharmaceutical composition of claim 2, wherein the pharmaceutical composition induces chemical castration in patients with advanced prostate cancer.

* * * * *

UNITED STATES PATENT AND TRADEMARK OFFICE
CERTIFICATE OF CORRECTION

Page 1 of 1

PATENT NO. : 10,166,181 B2
APPLICATION NO. : 12/601649
DATED : January 1, 2019
INVENTOR(S) : Ducrey et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 389 days.

Signed and Sealed this
Twenty-eighth Day of January, 2020

Andrei Iancu
*Director of the United States Patent and Trademark Office*